(12) United States Patent
Guo et al.

(10) Patent No.: US 11,047,789 B2
(45) Date of Patent: Jun. 29, 2021

(54) IRREGULAR ROCK SAMPLE HIGH-PRESSURE PERMEATION DEVICE WITH ADJUSTABLE FLOW DIRECTION AND TEST METHOD THEREOF

(71) Applicant: SOUTHWEST PETROLEUM UNIVERSITY, Sichuan (CN)

(72) Inventors: Liang Guo, Sichuan (CN); Junwei Zhang, Sichuan (CN); Ziwei Xiao, Sichuan (CN); Baoquan Wang, Sichuan (CN); Mingwei Liao, Sichuan (CN); Deliang Qian, Sichuan (CN); Chun Pei, Sichuan (CN); Youjun Ji, Sichuan (CN); Jiao Zhu, Sichuan (CN); Hui Guo, Sichuan (CN); Zhuangzhi Liu, Sichuan (CN)

(73) Assignee: SOUTHWEST PETROLEUM UNIVERSITY, Sichuan (CN)

( * ) Notice: Subject to any disclaimer, the term of this patent is extended or adjusted under 35 U.S.C. 154(b) by 93 days.

(21) Appl. No.: 16/581,770

(22) Filed: Sep. 25, 2019

(65) Prior Publication Data
US 2020/0018681 A1 Jan. 16, 2020

(30) Foreign Application Priority Data
Aug. 2, 2019 (CN) .......................... 201910712083.X

(51) Int. Cl.
*G01N 15/08* (2006.01)
*G01N 33/18* (2006.01)
*G01N 33/24* (2006.01)

(52) U.S. Cl.
CPC ....... *G01N 15/082* (2013.01); *G01N 15/0806* (2013.01); *G01N 33/18* (2013.01); *G01N 33/24* (2013.01)

(58) Field of Classification Search
CPC .. G01N 15/082; G01N 15/0806; G01N 33/18; G01N 33/24; G01N 2203/0256
See application file for complete search history.

(56) References Cited

U.S. PATENT DOCUMENTS 2,842,958 A * 7/1958 Roark ................ G01N 15/0806
73/38
3,616,685 A * 11/1971 Strom ...................... G01N 3/02
73/84

(Continued)

FOREIGN PATENT DOCUMENTS

CN 205786624 U 12/2016
CN 105928741 B 1/2019

(Continued)

OTHER PUBLICATIONS

Guo, Liang. (2018). Experimental study of hydraulic characteristics of undisturbed fractured rock in granite fault zone. Yantu Lixue/ Rock and Soil Mechanics. 3937-3948.

(Continued)

*Primary Examiner* — David A. Rogers

(57) ABSTRACT

An irregular rock sample high-pressure permeation device with an adjustable flow direction and a test method thereof are provided, wherein two blocking mechanisms I and two blocking mechanisms II are arranged inside a cylinder body; partitioning plates are respectively arranged on both sides of each of the blocking mechanisms I; water blocking plates are respectively arranged at both sides of each of the blocking mechanisms I; one end of each of the water blocking plates is connected to the sidewall of each of the partitioning plates, and the other end of each of the water blocking plates is connected to an internal portion of the cylinder body; a water injection pipe is disposed between the water blocking plates on a same side. The present invention (Continued)

combines flexible film amorphous close fit properties and easy charging and discharging of free gas.

8 Claims, 7 Drawing Sheets

(56)  References Cited

U.S. PATENT DOCUMENTS

| | | | | |
|---|---|---|---|---|
| 4,502,338 A * | 3/1985 | Smith | | G01N 3/08 73/819 |
| 4,599,891 A * | 7/1986 | Brauer | | G01N 15/0806 73/38 |
| 4,688,238 A * | 8/1987 | Sprunt | | G01N 23/046 378/210 |
| 4,710,948 A * | 12/1987 | Withjack | | G01N 23/04 378/208 |
| 4,799,382 A * | 1/1989 | Sprunt | | G01N 15/088 378/4 |
| 4,825,700 A * | 5/1989 | Vardoulakis | | G01N 3/08 73/749 |
| 4,979,390 A * | 12/1990 | Schupack | | G01M 3/04 73/38 |
| 5,025,668 A * | 6/1991 | Sarda | | G01N 3/10 73/795 |
| 5,065,421 A * | 11/1991 | Morineau | | G01N 15/0806 378/208 |
| 5,159,828 A * | 11/1992 | Steiger | | E21B 49/006 73/38 |
| 5,226,310 A * | 7/1993 | Steiger | | E21B 49/006 73/38 |
| 5,269,999 A * | 12/1993 | Smesny | | B29C 43/18 264/112 |
| 5,275,063 A * | 1/1994 | Steiger | | G01N 33/241 73/865.6 |
| 5,285,692 A * | 2/1994 | Steiger | | E21B 49/005 73/866 |
| 5,363,692 A * | 11/1994 | Lafargue | | G01N 33/241 73/38 |
| 5,563,333 A * | 10/1996 | Haines | | G01N 15/0806 73/38 |
| 5,606,133 A * | 2/1997 | Hines | | B29C 43/04 73/818 |
| 5,698,772 A * | 12/1997 | Deruyter | | G01N 15/0826 73/38 |
| 5,739,436 A * | 4/1998 | Trautwein | | G01N 3/24 73/841 |
| 5,979,223 A * | 11/1999 | Fleury | | G01N 33/241 73/38 |
| 6,026,692 A * | 2/2000 | Brovoid | | B29C 43/04 73/818 |
| 6,729,189 B2 * | 5/2004 | Paakkinen | | G01N 3/02 73/813 |
| 6,971,260 B2 * | 12/2005 | Potter | | G01N 3/10 73/38 |
| 7,143,653 B2 * | 12/2006 | Abdel-Hadi | | G01N 3/10 73/819 |
| 7,549,315 B2 * | 6/2009 | Bulled | | G01N 3/10 73/11.01 |
| 7,793,552 B2 * | 9/2010 | Ng | | G01N 33/24 73/818 |
| 8,234,912 B2 * | 8/2012 | Suarez-Rivera | | G01N 15/0826 73/81 |
| 8,375,802 B2 * | 2/2013 | Khoury | | G01N 33/24 73/784 |
| 8,438,914 B2 * | 5/2013 | Martiska | | G01N 3/08 73/84 |
| 8,561,474 B2 * | 10/2013 | Secq | | G01N 3/10 73/825 |
| 8,650,948 B2 * | 2/2014 | Lee | | G01F 1/00 73/219 |
| 8,770,038 B2 * | 7/2014 | Secq | | G01N 3/24 73/821 |
| 8,800,353 B2 * | 8/2014 | Ng | | G01N 13/04 73/73 |
| 9,316,572 B2 * | 4/2016 | Benet | | G01N 3/08 |
| 9,546,940 B2 * | 1/2017 | Gupta | | G01N 33/24 |
| 9,863,925 B2 * | 1/2018 | Gerber-Siff | | G01N 33/24 |
| 9,903,826 B2 * | 2/2018 | Alshehri | | G01N 23/20025 |
| 9,921,202 B2 * | 3/2018 | Huang | | G01N 33/24 |
| 10,145,775 B2 * | 12/2018 | Savari | | G01N 33/24 |
| 10,190,413 B2 * | 1/2019 | Smith | | H01J 49/0468 |
| 10,324,227 B2 * | 6/2019 | Yang | | G01V 9/005 |
| 10,365,193 B2 * | 7/2019 | Feng | | G01N 3/12 |
| 10,472,788 B2 * | 11/2019 | Wang | | E02D 3/10 |
| 10,712,253 B2 * | 7/2020 | Su | | G01N 15/082 |
| 10,801,934 B2 * | 10/2020 | Liu | | G01N 3/18 |
| 10,801,942 B2 * | 10/2020 | Ou | | G01N 33/241 |
| 10,845,291 B2 * | 11/2020 | Kanj | | G01N 33/241 |
| 2004/0244497 A1 * | 12/2004 | Abdel-Hadi | | G01N 3/10 73/819 |
| 2005/0150273 A1 * | 7/2005 | Potter | | G01N 3/10 73/38 |
| 2008/0257030 A1 * | 10/2008 | Slavin | | G01N 15/08 73/152.11 |
| 2009/0049924 A1 * | 2/2009 | Ng | | G01N 33/24 73/818 |
| 2011/0132099 A1 * | 6/2011 | Secq | | G01N 3/24 73/821 |
| 2011/0214506 A1 * | 9/2011 | Khoury | | G01N 33/24 73/784 |
| 2013/0002258 A1 * | 1/2013 | Ligneul | | E21B 47/06 324/376 |
| 2013/0054157 A1 * | 2/2013 | Lasseux | | G01N 15/0826 702/47 |
| 2013/0104629 A1 * | 5/2013 | Oh | | G01N 15/0826 73/38 |
| 2014/0116114 A1 * | 5/2014 | Lee | | G01N 15/082 73/38 |
| 2015/0267370 A1 * | 9/2015 | Gupta | | E02D 1/027 73/818 |
| 2017/0003263 A1 * | 1/2017 | Huang | | G01L 15/00 |
| 2018/0335374 A1 * | 11/2018 | Kanj | | G01N 15/0826 |
| 2018/0340873 A1 * | 11/2018 | Zhang | | G01N 3/10 |
| 2018/0340874 A1 * | 11/2018 | Liu | | G01N 3/18 |
| 2019/0011344 A1 * | 1/2019 | Zhou | | G01N 3/10 |
| 2019/0011422 A1 * | 1/2019 | McGregor | | E21B 43/11 |
| 2019/0187039 A1 * | 6/2019 | Su | | G01N 33/24 |
| 2019/0234856 A1 * | 8/2019 | Ou | | G01N 15/082 |
| 2019/0331569 A1 * | 10/2019 | Liu | | G01N 3/062 |
| 2020/0080924 A1 * | 3/2020 | Zhou | | E21B 49/088 |
| 2020/0217193 A1 * | 7/2020 | Li | | E21B 21/08 |
| 2020/0284712 A1 * | 9/2020 | Gou | | E21B 49/02 |

FOREIGN PATENT DOCUMENTS

| CN | 105928764 B | 1/2019 |
|---|---|---|
| CN | 105928858 B | 1/2019 |

OTHER PUBLICATIONS

Guo, Liang & Hu, XW. (2018). Simulation of Fluid Flow in Fractured Rocks Based on the Discrete Fracture Network Model Optimized by Measured Information. International Journal of Geomechanics. 18. 10.1061/(ASCE) GM.1943-5622.0001270.

Guo, Liang & Li, Xiaozhao & Zhou, Yangyi & Zhang, Yangsong. (2015). Generation arid verification of three-dimensional network of fractured rock masses stochastic discontinuities based on digitalization. Environmental Earth Sciences. 73. 10.1007/s12665-015-4175-3.

* cited by examiner

IRREGULAR ROCK SAMPLE HIGH-PRESSURE PERMEATION DEVICE WITH ADJUSTABLE FLOW DIRECTION AND TEST METHOD THEREOF

CROSS REFERENCE OF RELATED APPLICATION

The present invention claims priority under 35 U.S.C. 119(a-d) to CN 201910712083.X, filed Aug. 2, 2019.

BACKGROUND OF THE PRESENT INVENTION

Field of Invention

The present invention relates to the characterization and evaluation of groundwater flow characteristics for key water-conducting geological structures in engineering rock masses such as rock slopes and mountain tunnels, and more particularly to an in-door high-pressure seepage device for comprehensively characterizing hydrogeological properties of water-conducting structures by quantitatively measuring permeability parameters of an intersecting fracture network in an irregular rock sample. The present invention provides an effective means for analyzing groundwater flow characteristics of regional rock masses in laboratory, and is also a useful exploration for difference analysis of water conductivity of geological structures under different seepage pathways, which provides a new research idea for spatial variability analysis of hydraulic parameters of fractured rock masses. The present invention is generally applicable to the evaluation of groundwater flow characteristics for irregular fractured rock, and is especially suitable for characterizing hydrogeological properties of key water-conducting and water-control geological structures in environmental and energy engineering fields such as geological disposal of high-level radioactive waste, development of shallow underground space, and deep geothermal energy exploitation, providing reliable indicators for regional groundwater flow characteristics assessment.

Description of Related Arts

The rock mass is a non-uniform and anisotropic medium with complex mechanics and hydraulic properties. The groundwater in the rock masses often occurs in the fractures and migrates along the intersecting fracture network. It can be seen that the seepage properties of the fracture network often determine flow characteristics of the regional groundwater, thereby affecting the solute transport and contaminant dispersion, and even causing rock slope sliding and underground cavern collapse. The migration and dispersion of ground contaminant to underground with the seepage will cause a large-scale area of groundwater pollution. The permeation of surface water into the high-level radioactive waste repository will communicate the hydraulic relationship between the nuclear waste and the groundwater, which will cause nuclear pollution in the regional groundwater environment. It can be seen that the safety of major environmental and energy projects such as geological disposal of high-level radioactive waste, geothermal energy development, and oil exploitation are closely related to regional groundwater flow. Therefore, the characterization and evaluation of groundwater flow characteristics in key water-conducting geological structures of regional rock masses have important theoretical research significance and engineering application value.

The natural rock mass has a lot of fractures with different sizes and directions due to the geological processes including tectonic movement, weathering effect and unloading effect. The fractures are interwoven in the rock masses to form an intersecting fracture network. Geological structures such as faults and folds contain abundant fracture networks, which usually guide and control the regional groundwater flow. However, Different types of geological structures have different water-conducting/controlled features. For example, the occurrence and migration patterns of the groundwater in fractures with different scales, forms and connecting conditions are significantly different. The new fault may have higher permeability because it has not been "closed" yet. The groundwater flow characteristics of faults with similar fracture density may be significantly different; some superior water bearing faults may control groundwater flow patterns; and groundwater flowing through different seepage pathways may exhibit distinct migration modes. Therefore, quantitatively characterization of hydrogeological attributes and flow characteristics of key geological structures, and difference analysis of water-conductivity of geological structures under different seepage pathways are vital for prevention and control of landslide, stability estimation of underground cavern and prediction of contaminants dispersion.

SUMMARY OF THE PRESENT INVENTION

An object of the present invention is to provide an irregular fracture in-door high-pressure permeation device with a freely adjustable flow direction and a test method thereof for multi-directional seepage test for large-volume irregular rock samples with rich geological structure information under a confining pressure condition, so as to quantitatively obtain permeability parameters of an intersecting fracture network, analyze the difference of water conductivity of geological structures under different seepage pathways, and comprehensively characterize hydrogeological properties of geological structures, thereby providing a reliable indicator for regional groundwater flow characteristics assessment. Accordingly, in order to accomplish the above object, the present invention provides:

an irregular rock sample high-pressure permeation device with an adjustable flow direction, comprising: a cylinder body having a top opening, and a sealing cover matched with the top opening of the cylinder body, wherein two blocking mechanisms I are symmetrically arranged in the cylinder body along an axis thereof, and two blocking mechanisms II are respectively arranged at an internal top end and an internal bottom end of the cylinder body; partitioning plates, whose bottom ends are connected to a bottom of the cylinder body, are respectively arranged on both sides of each of the blocking mechanisms I; one end of a sealing organ cover is connected to a sidewall of each of the partitioning plates, and the other end of the sealing organ cover is connect a sidewall of each of the blocking mechanisms I; water blocking plates are respectively arranged at both sides of each of the blocking mechanisms I and are perpendicular to the partitioning plates; one end of each of the water blocking plates is connected to the sidewall of each of the partitioning plates, and the other end of each of the water blocking plates is connected to an internal portion of the cylinder body; a water injection pipe is disposed between the water blocking plates on a same side, and an end of the water injection pipe extends outwardly through an internal wall of the cylinder body; during utilization, a rock sample is placed in the cylinder body, and the two blocking mechanisms I and the two blocking mechanisms II are adjusted to block four sidewalls of the irregular rock sample, while two sides of the irregular rock sample, which face the water injection pipe, are not blocked.

In the prior art, because the laboratory seepage test link is extremely demanding on the sealing of the non-permeable boundaries of the rock sample, the conventional in-door seepage test instrument is only suitable for cylindrical regular sample test (which is convenient to blocking and the technique is developed), or irregular sample test (using cured colloid to seal non-permeable boundary to permanently and efficiently block water) with a fixed flow direction (because the colloidal seal is irreversible, and the direction of seepage and permeation is irreversible). It is unable to meet the requirements of water conductivity difference analysis under different seepage pathways, and it is difficult to objectively obtain the spatial variability of hydraulic parameters of key geological structures. Therefore, how to effectively realize the reversible sealing of irregular boundaries, how to freely convert the sealing state (sealed or permeable) of large-scale boundaries, and how to accurately adjust the stress conditions of the seepage environment for large-scale irregular rock samples from the site containing rich geological structure information, are difficult problems to be solved in front of scientific researchers. In view of the above situation, the applicant designed a permeation test device for irregular undisturbed fractured rock, which can effectively block multiple end faces of the rock sample, and the blocking process is reversible. That is to say, the six end faces of the rock sample can be successively permeated. After the two test end faces of the rock sample are selected, sodium fluorescein is injected into a permeating fluid, and the fluorescent water flow is observed on the sidewall based on the fluorescent trace effect, so as to achieve the objective judgment of sidewall leakage and the objective evaluation of the reliability of the result. In practice, the cylinder body and the sealing cover matched with the cylinder body can form a confined space for injecting water and applying pressure to the rock sample. After the rock sample is put into the cylinder body, positions of the two blocking mechanisms I and the two blocking mechanisms II in the cylinder body are adjustable and can correspond to the four non-permeable surfaces of the rock sample. The two partitioning plates and two sidewalls of the blocking mechanism I are sealed by the sealing organ cover, and the two water blocking plates on both sides of the water injection pipe provide independent flow pathways for the water. Water can penetrate from one test end to another test end face, and test end faces of the rock sample can be replaced just by flipping and adjusting the position of the rock sample, which finally ensures the test data obtained by the permeation test is accurate and comprehensive.

Each of the blocking mechanisms I comprises a shell having a cavity therein, wherein an opening is provided on a sidewall of the shell; each of the blocking mechanisms II comprises a tank having a cavity therein, wherein a through hole is provided on a sidewall of the tank; film assemblies are disposed inside the shell as well as the tank, comprising a positive rotation shaft, a driving cylinder, two longitudinal conveyor belts and two transverse conveyor belts, wherein a water blocking film is wound around an external circumferential wall of the positive rotation shaft, and the longitudinal conveyor belts are perpendicular to the transverse conveyor belts; a first slider is fixed on each of the longitudinal conveyor belts, a second slider is fixed on each of the transverse conveyor belts, a first chuck is fixed on the first slider, and a second chuck is fixed on the second slider; an output end of the driving cylinder is provided with a rectangular frame; the positive rotating shaft is rotatably disposed at a top of an internal wall of the shell; the two longitudinal conveyor belts are located at two sides of the opening or the through hole, and a movable end of the water blocking film gradually closes the opening or the through hole with clamping of the first chuck on each of the longitudinal conveyor belts; when the movable end of the water blocking film is moved to a horizontal position corresponding to the transverse conveyor belts, the first chuck on each of the longitudinal conveyor belts releases the water blocking film, while the second chuck on each of the transverse conveyor belts clamps the water blocking film and moves the water film away from the opening or the through hole; then the driving cylinder is started, and the output end of the driving cylinder drives the rectangular frame to press the water blocking film, so as to seal the opening or the through hole;

a connecting tube is disposed on a sidewall of the shell facing the opening, and the connecting tube extends outwardly through the internal wall of the shell; an electromagnetic valve is mounted on an extended end of the connecting tube; a sleeve II is mounted on an external circumferential wall of the cylinder body, which communicates with the internal portion of the cylinder body; an intake pipe I moves through the sleeve II and is connected to the electromagnetic valve;

a communication tube is disposed on a sidewall at a top of the internal portion of the cylinder body, and the communication tube extends outwardly through an internal wall of the tank; the electromagnetic valve is also mounted on an extended end of the communication tube; a sleeve I is mounted on a top end surface of the cylinder body, which communicates with the internal portion of the cylinder body; an intake pipe II moves through the sleeve I and is connected to the electromagnetic valve;

a straight tube is disposed on a sidewall at a bottom of the internal portion of the cylinder body, and the straight tube extends outwardly through the internal wall of the tank; a flexible hose is connected to an extended end of the straight tube; and the flexible hose extends outwardly through an external wall of the cylinder body;

two push cylinders are horizontally placed in the shell, and an output end of each of the push cylinders is mounted with a push plate perpendicular to the longitudinal conveyor belts; wherein a length of the push plate equals to a width of the opening, and an interval between two push plates equals to a length of the opening.

Preferably, when the blocking mechanisms I and the blocking mechanisms II block the rock sample, the water blocking film is mainly applied to the non-permeable surfaces of the rock sample, and then the air pressure is synchronously added to the shell or the tank to ensure that the water blocking film and the non-permeable surfaces are completely adhered to achieve seepage-proofing of the non-permeable surface. It should be noted that the structures of the blocking mechanisms I and the blocking mechanisms II are substantially the same, such as the same size of the shell and the tank, as well as the corresponding size of the opening and the through hole. In practice, the film assemblies are provided in the blocking mechanisms I and the blocking mechanisms II. The film assembly of the blocking mechanisms I, for example, comprises the positive rotation shaft, the driving cylinder, the two longitudinal conveyor belts and the two transverse conveyor belts, wherein the two longitudinal conveyor belts are disposed on both side of the opening, and the two transverse conveyor belts are disposed on the internal wall at the bottom of the shell; the water blocking film is wound around the positive rotation shaft, and two sides thereof are respectively clamped through the first chucks of the two longitudinal conveyor belts, so that the water blocking film gradually seals the opening. When the water blocking film moves to the bottom of the shell and the movable end of the water blocking film is moved to the horizontal position corresponding to the transverse conveyor belts, the first chuck on each of the longitudinal conveyor belts releases the water blocking film, while the second chuck on each of the transverse conveyor belts clamps the water blocking film and moves the water blocking film away from the opening or the through hole; then the two horizontally placed push cylinders are started, wherein the length of the push plate equals to the width of the opening, which can drive the water blocking film to extend outwardly through the opening. The extended portion of the water blocking film can directly cover the top end surface and the bottom end surface of the rock sample. Then the driving cylinder is started, and the output end of the driving cylinder drives the rectangular frame to press the water blocking film until the rectangular frame drives the water blocking film to closely adhere to the internal wall of the shell, so as to seal the opening. At this time, the two ends of the rock sample are respectively supported by two openings. After position adjustment of the blocking mechanisms II located at the top and bottom ends of the rock sample, the internal film assembly starts to perform a filming action, and the film assembly in the blocking mechanisms II performs the same action as that performed by the film assembly in the block mechanisms I, both close the through holes by the water blocking film driven by the chucks on the two longitudinal conveyor belts and the transverse lateral conveyor belts. Then the driving cylinder in the tank is started, and the output end of the driving cylinder drives the rectangular frame to press the water blocking film until the rectangular frame drives the water blocking film to closely adhere to the internal wall of the tank, so as to seal the through hole.

And the connecting tube is disposed on the sidewall of the shell facing the opening, and the connecting tube extends outwardly through the internal wall of the shell; the electromagnetic valve is mounted on an extended end of the connecting tube; a sleeve II is mounted on an external circumferential wall of the cylinder body, which communicates with the internal portion of the cylinder body; an intake pipe I moves through the sleeve II and is connected to the electromagnetic valve; a communication tube is disposed on a sidewall at a top of the rock sample, and the communication tube extends outwardly through an internal wall of the tank; the electromagnetic valve is also mounted on an extended end of the communication tube; a sleeve I is mounted on a top end surface of the cylinder body, which communicates with the internal portion of the cylinder body; an intake pipe II moves through the sleeve I and is connected to the electromagnetic valve; a straight tube is disposed on a sidewall at a bottom of the internal portion of the cylinder body, and the straight tube extends outwardly through the internal wall of the tank; a flexible hose is connected to an extended end of the straight tube, and the flexible hose extends outwardly through an external wall of the cylinder body. After driving the intake pipe I and the intake pipe II to move, the two shells and the tank above the rock sample can be linearly moved to adjust the position thereof, so as to match a shape of the rock sample to a maximum extent.

Meanwhile, the tank below the rock sample remains stationary, and after the four water blocking films respectively contact with the four non-permeable surfaces of the rock sample, gas is simultaneously injected into the intake pipe I, the intake pipe II, and the hose, so that internal air pressures of the tank and the shell are increased to ensure that the water blocking film is in close contact with each non-permeable surface. After the above steps are completed, water is injected into any one of the water injection pipes, and the other water injection pipes are kept closed until the water level in the cylinder body exceeds the bottom end of the tank above, and then the penetration test begins.

Preferably, when the water blocking film inside the two shells covers the sidewalls of the rock sample, under the pushing action of the push plate, the extended portion of the water blocking film can partially cover the top and bottom end faces of the rock sample, while the water blocking film at the two through holes covers the top and bottom end surfaces of the rock sample for the second time. At the same time, blocking effects on the four non-permeable surfaces of the rock sample are improved through extrusion of the air pressure in the tank.

A pressing frame I is disposed on the output end of the driving cylinder inside the shell, and the pressing frame I is a rectangular bracket formed by splicing four L-shaped plates; a telescopic cylinder is mounted on one end surface of each of the L-shaped plates, and a connecting rod is fixed on the other end surface; among adjacent L-shaped plates, an output end of the telescopic cylinder of one L-shaped plate is connected to the connecting rod of the other L-shaped plate; a supporting rod is respectively mounted on a sidewall of each of the L-shaped plates, and the supporting rod is connected to the output end of the driving cylinder;

a pressing frame II is disposed on the output end of the driving cylinder inside the tank, and the pressing frame II is a U-shaped bracket formed by splicing two symmetrically distributed L-shaped plates; the telescopic cylinder is mounted on an end surface of a horizontal section of one L-shaped plate, and the connecting rod is mounted on an end surface of a horizontal section of the other L-shaped plate; the output end of the telescopic cylinder is connected to the connecting rod; a vertical end face of each of the L-shaped plates is provided with a pressing rod, and the pressing rod is perpendicular to a vertical section of the L-shaped plates; a strut is provided on any one of the L-shaped plates, and is connected to the output end of the driving cylinder. Moreover, since edges of the square rock sample are not straight lines, the applicant provides the pressing frame I and the pressing frame II respectively in the shell and the tank, which means the pressing frame I corresponds to the rectangular bracket and the pressing frame II corresponds to the U-shaped bracket. When the water blocking film blocks the four non-permeable surfaces, the rectangular bracket and the U-shaped bracket can drive the water blocking film to completely wrap the non-permeable surfaces, and can expand and contract to a certain amplitude, so as to allow corner portions of the two end faces to be tested of the rock sample to be wrapped by the water blocking film to prevent water penetrating along the non-permeable surfaces; thereby ensuring the accuracy of the test data. In practice, the rectangular frame and the rectangular bracket are both fixed on the output end of the driving cylinder in the shell, and an interval between the rectangular bracket and the opening is smaller than an interval between the rectangular frame and the opening. That is to say, when the driving cylinder is started, the rectangular bracket first drives the water blocking film to pass through the opening and then to be sleeved at an end of the rock sample, wherein the rectangular bracket is formed by splicing four L-shaped plates, and among adjacent L-shaped plates, the output end of the telescopic cylinder of one L-shaped plate is connected to the connecting rod of the other L-shaped plate, which allows an operator to adjust length and width of the rectangular bracket according to an actual size of the rock sample, and to finally ensure that the rectangular bracket can drive the water blocking film to completely wrap the non-permeable surfaces of the rock sample to avoid permeation of the non-permeable surfaces. The rectangular frame and the U-shape bracket are both fixed on the output end of the driving cylinder in the tank, and an interval between the U-shape bracket and the opening is smaller than an interval between the rectangular frame and the opening. That is to say, when the driving cylinder is started, the rectangular bracket first drives the water blocking film to pass through the opening and then to be sleeved at an end of the rock sample, wherein the U-shape bracket is formed by splicing two L-shaped plates, and the telescopic cylinder is mounted on the end surface of the horizontal section of one L-shaped plate, and the connecting rod is mounted on the end surface of the horizontal section of the other L-shaped plate; the output end of the telescopic cylinder is connected to the connecting rod; the vertical end face of each of the L-shaped plates is provided with the pressing rod, and the pressing rod is perpendicular to the vertical section of the L-shaped plates. Similarly, the operator can adjust an interval between the pressing rod according to the actual size of the rock sample, to finally ensure that the U-shape bracket can drive the water blocking film to completely wrap the non-permeable surfaces of the rock sample to avoid permeation of the non-permeable surfaces.

The first chuck comprises a U-shaped body and two flexible splints, wherein blind holes are drilled on sidewalk corresponding to two vertical sections of the U-shaped body; a pin is mounted on one sidewall of each of the flexible splints, and an electromagnet is embedded in a middle of the other sidewall of each of the flexible splints; a gap is left between an end face of the pin and a bottom of the blind hole, and a torsion spring is sleeved on an external circumferential wall the pin; one end of the torsion spring is connected to the external circumferential wall of the pin, and the other end of the torsion spring is connected to the bottom of the blind hole. Moreover, a function of the chuck is to move the water blocking film along a fixed track in a lateral direction or a longitudinal direction, and since the water blocking film belongs to a flexible material, the chuck should provide sufficient clamping force while ensures accurate clamping or releasing of the water blocking film. Therefore, the applicant sets the U-shaped body and the two flexible splints. In an initial state, the two flexible splints are in contact with each other, and the torsion spring is in a free state. When the chuck needs to be contacted to hold the water blocking film, the electromagnets on the two flexible splints are simultaneously energized to have same magnetic poles, wherein repulsive force is generated between the two electromagnets, so that the flexible splints press and compress the torsion spring, and an interval between the two flexible splints is increased, which means the chuck releases the water blocking film. The electromagnet is turned on and off to provide smooth transition from longitudinal movement to lateral movement of the water block film, avoiding a situation that the four chucks simultaneously clamp and pull the water blocking film during use. Water blocking film integrity throughout the test is ensured.

Two guide rails are fixed on the internal wall of the cylinder body, and each of the guild rails is respectively located between the partitioning plates of a same side; a sliding groove is provided on a top surface of each of the guide rails, and a guiding block cooperating with the sliding groove is provided at a bottom of the shell. Preferably, since the two shells need to be positionally adjusted before the test, that is, the shell will move linearly, the guide rails are fixed inside the cylinder body by the applicant to improve stability of the shell movement, and each of the guild rails is respectively located between the partitioning plates of the same side; the sliding groove is provided on the top surface of each of the guide rails, and the guiding block cooperating with the sliding groove is provided at the bottom of the shell. The guiding block can only move along a trajectory where the sliding groove is located, which lowers a possibility of shell sloshing and ensures shell stability when it is adjusted from an initial position to a final state, thereby ensuring the sealing effect on the four non-permeable surfaces of the rock sample.

A rubber pad having an arcuate cross section is provided on each internal sidewall of the rectangular frame. Preferably, the rubber pad having the arcuate cross section is provided on each internal sidewall of the rectangular frame, so that the rectangular frame realizes flexible contact when the water blocking film is wrapped around the rock sample, and reduces mutual damages between the water blocking film and the rock sample when the rectangular frame contracts.

A circular bottom plate is disposed at a bottom portion of the internal wall of the cylinder body, and the circular bottom plate divides the internal portion of the cylinder body into an adjustment zone and a test zone which are independent; an up-push cylinder is disposed in the adjustment zone, and a ram is provided at an output end of the up-push cylinder; a small hole is opened in a middle of the circular bottom plate, and a waterproof ring is installed in the small hole; a top end of the ram moves through the waterproof ring and then is connected to an external wall of the blocking mechanisms II located at a bottom of the test zone. Moreover, after being placed in the cylinder body, the rock sample is supported by the blocking mechanisms II at the bottom of the cylinder body. And before testing, relative positions of the two blocking mechanisms I and the two blocking mechanisms II need to be adjusted to ensure the blocking effect of the four non-permeable surfaces the rock sample. When the blocking mechanisms II located at the bottom of the cylinder body are lifted or lowered, only the up-push cylinder is activated, and the top end of the ram at the output end of the up-push cylinder moves through the waterproof ring and then is connected to an external wall of the blocking mechanisms II located at a bottom of the test zone. When the output end of the up-push cylinder drives the ram to move, the tank can be driven to move linearly. The waterproof ring is a waterproof rubber ring. Under the premise of relative motion between the waterproof rubber ring and the ram, the independence between the test zone and the adjustment zone can be ensured.

A test method of an irregular rock sample high-pressure permeation device with an adjustable flow direction is also provided, comprising steps of:

a) clearing soil and fragmented rocks deposited by weathering and erosion on a surface of a rock mass to be investigated, excavating vertical trenches around a target point, and exposing a fresh geological body to be inspected;

b) using a joint structure analysis method together with a geophysical detection method to extract fracture intersection information inside the geological body exposed in the step a), and identifying water-conducting units and water-control nodes which conduct and control a groundwater flow;

c) based on an identification result of the step b), marking four to five sampling ranges on the geological body to be inspected which is obtained in the step a), and intercepting large-volume irregular undisturbed rock samples containing a plurality of the water-conducting units and water-control nodes along each sampling boundary;

d) determining four to five seepage test directions for the rock samples obtained in the step c), and defining two opposite boundaries along a sample seepage direction as permeable interfaces A and B, wherein A is an in-permeation surface, B is an out-permeation surface, and other sample boundary surfaces are defined as non-permeable surfaces;

e) loading one of the rock samples in the step d) into a cylinder body according to a position meeting a predetermined seepage direction, in such a manner that the in-permeation surface and the out-permeation surface of the rock sample respectively correspond to two open end faces of the cylinder body; blocking the non-permeable surfaces by two blocking mechanism I and two blocking mechanisms II;

t) waiting until an anti-seepage blocking treatment in the step e) is completed, then sealing the open ends of the cylinder body by sealing covers to form a seepage pressure chamber;

g) connecting an in-permeation surface of the seepage pressure chamber to a pressurized water supply equipment through a water injection pipe, and connecting an out-permeation surface to a water storage container through another water injection pipe, so as to assemble an irregular rock sample high-pressure permeation tester;

h) after components in the step g) are completely connected, staring a pressure measuring device to apply an osmotic water pressure to the rock sample when air pressures in two shells and two tanks reach a steady state, wherein water continuously flows along a fracture network of the rock sample from the in-permeation surface under a preset initial pressure, so as to achieve sample saturation;

i) adjusting an osmotic pressure value of the pressure measuring equipment, and recording corresponding data comprising pressures, times and flow rates after water flow reaches a steady state; further changing a confining pressure and the osmotic pressure value according to a predetermined plan in an experimental scheme, to obtain a group of steady-state test data corresponding to different confining pressures and different osmotic pressures;

j) opening the sealing covers, and releasing the two blocking mechanisms I and the two blocking mechanisms II to free the non-permeable surfaces of the rock sample; turning the rock sample, and redefining the non-permeable surfaces, the in-permeation surface and the out-permeation surface of the rock sample according to the seepage test directions determined in the step d); repeating the steps e)-i) until the rock sample seeps through all the predetermined seepage test directions;

k) repeating the steps d)-j) for the other of the rock samples obtained in the step c) until all the rock samples are tested; and l) calculating and analyzing based on data obtained in the step k) to obtain spatial variability of a water-conducting structure of a geological structure under different seepage pathways, and further obtain comprehensive characterization results of hydrogeological properties of the geological structure.

It should be further pointed out that in the step b), the joint structure analysis method refers to a method for analyzing and interpreting the internal structural features of the geological body and its evolution, focusing on the analysis of the geometric features, hydraulic properties and mutual relations of various structural elements. The geophysical detection method comprises borehole ultrasonic detection, geological radar detection, etc. Among them, borehole ultrasonic detection uses acoustic transducers to compare and analyze acoustic spectrum, wave velocity and attenuation characteristics, so as to detect rock fragmentation, fracture distribution characteristics and spatial variability.

In the step e), the two blocking mechanisms I and the two blocking mechanisms II block the non-permeable surfaces of the rock sample. After the four water blocking films are respectively in contact with the four non-permeable surfaces of the rock sample, gas is simultaneously injected into the intake pipe I, the intake pipe II, and the hose, so that internal air pressures of the tank and the shell are increased to ensure that the water blocking film is in close contact with each non-permeable surface. The internal air pressures in the tank and the shell are ranged at 0-1 MPa and then are defined as the confining pressures.

The pressurized water supply equipment used in the present invention is a conventional technical product in the prior art, and the main operating parameters thereof are: a constant pressure differential controlled seepage flow mode is used, a pressure control range is 0-1 MPa, a control precision is ±1 kPa, a volume measurement range is 0-1500 ml, and a measurement accuracy is ±1% FS. The seepage test method adjusts the osmotic pressure by the pressurized water supply equipment, and records the corresponding pressure and flow data after the water flow reaches a steady state.

Compared with the prior art, the present invention has the following advantages and beneficial effects:

1. The present invention can realize effective sealing of a plurality of non-permeable surfaces of the irregular rock samples, which combines flexible film amorphous close fit properties and easy charging and discharging of free gas, so as to realize the high-pressure sealing of the irregular boundary and the reversible water permeability condition. By transforming the placement orientation of the rock sample, the six end faces are alternately set as the out-permeation or the in-permeation surface to realize the rock sample test under different seepage pathways. The gas confining pressure is evenly applied to achieve the precise regulation of the stress state, and objectively obtain water conductivity difference analysis of geological structures and spatial variability characterization of hydraulic parameters.

2. The present invention has a propulsion cylinder corresponding to the propulsion shell on the internal wall of a fixing plate, which means a telescopic frequency of the output end of the propulsion cylinder is the same as the amplitude variation frequency generated by the eccentric wheel, wherein when the eccentric wheel generates a vertical upward amplitude, the output end of the propulsion cylinder moves downward to bring a pressure plate into contact with the top surface of the propulsion shell to eliminate vibration in the direction, thereby ensuring stability of the moving process of the shell and the bottom plate, and shortening a time consumption of a bottom jaw to convert from an initial state to a final state.

3. The present invention drills a limit slot on a sidewall of the sliding plate facing the sliding groove, and the size of the limit slot matches the bottom jaw. After a reinforcing cage is completely lowered to a pile hole, the bottom jaw is moved by a follower plate and turned down to the limit slot, which means the bottom jaw is completely out of contact with a hoop stirrup, and a hook is lifted to make a hanging rib gradually get out of the pile hole, thereby effectively avoiding any interference of the hoop stirrup on the smooth exit of an entire cylindrical frame from the pile hole.

4. The present invention effectively solves the problem that the conventional in-door seepage test instrument for large-volume irregular rock samples containing rich geological structure information from the site cannot quantitatively carry out the water conductivity difference analysis under different seepage pathways, and it is difficult to obtain spatial variability characterization of body hydraulic parameters of key geological structures. The present invention utilizes the film assembly having a high-pressure sealing function of irregular boundaries and a reversible conversion function of water-to permeable conditions, and transforming the placement orientation of the rock sample in a seepage pressure chamber, the six end faces are alternately set as the out-permeation or the in-permeation surface and seepage directions are manually changed, so as to realize the rock sample permeability test under different seepage pathways. The gas confining pressure is evenly applied to achieve the precise regulation of the seepage environment stress state, and objectively obtain water conductivity difference analysis of geological structures and spatial variability characterization of hydraulic parameters under an original stress state.

BRIEF DESCRIPTION OF THE DRAWINGS

The drawings are intended to provide a further understanding of the embodiments of the present invention, and are not intended to limit the embodiments of the present invention.

ELEMENT REFERENCE

1—sealing cover, 2—sleeve I, 3—electromagnetic valve, 4—blocking mechanism II, 5—side plate, 6—partitioning plate, 7—blocking mechanism I, 701—positive rotation shaft, 702—push cylinder, 703—water blocking film, 704—rectangular frame, 705—longitudinal conveyor belt, 706—push plate, 707—pressing frame I, 708—first slider, 709—first chuck, 710—opening, 711—driving cylinder, 712—pushing rod, 713—transverse conveyor belt, 714—second slider, 715—second chuck, 716—reverse rotation shaft, 717—electromagnet, 718—flexible splint, 719—torsion spring, 720—pin, 8—cylinder body, 9—sleeve II, 10—guide block, 11—guide rail, 12—circular bottom plate, 13—waterproof ring, 14—up-push cylinder, 15—intake pipe I, 16—connecting tube, 17—sealing organ cover, 18—water blocking plate, 19—water injection pipe, 20—communication pipe, 21—straight tube, 22—flexible hose, 23—pressing frame II, 24—L—shaped plate, 25—rubber pad, 26—telescopic cylinder, 27—connecting rod, 28—supporting rod, 29—strut, 30—pressing rod, 31—rock sample.

DETAILED DESCRIPTION OF THE PREFERRED EMBODIMENT

The present invention will be further described in detail below with reference to the embodiments and the accompanying drawings. The illustrative embodiments of the present invention and the description thereof are merely illustrative of the present invention and are not intended to be limiting.

Embodiment 1

Figure 1:
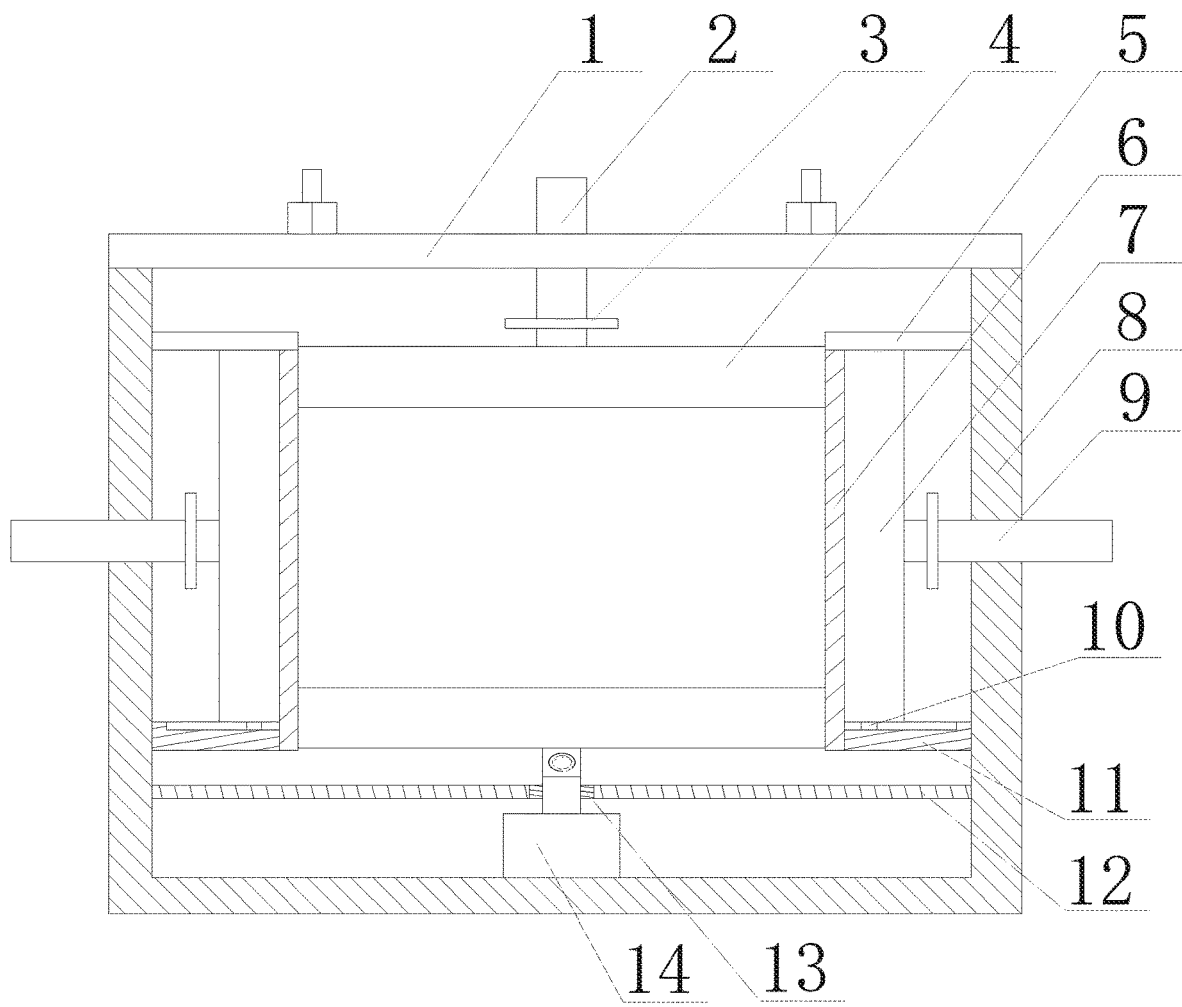
FIG. 1 is a longitudinal cross-sectional view of the present invention.
Figure 2:
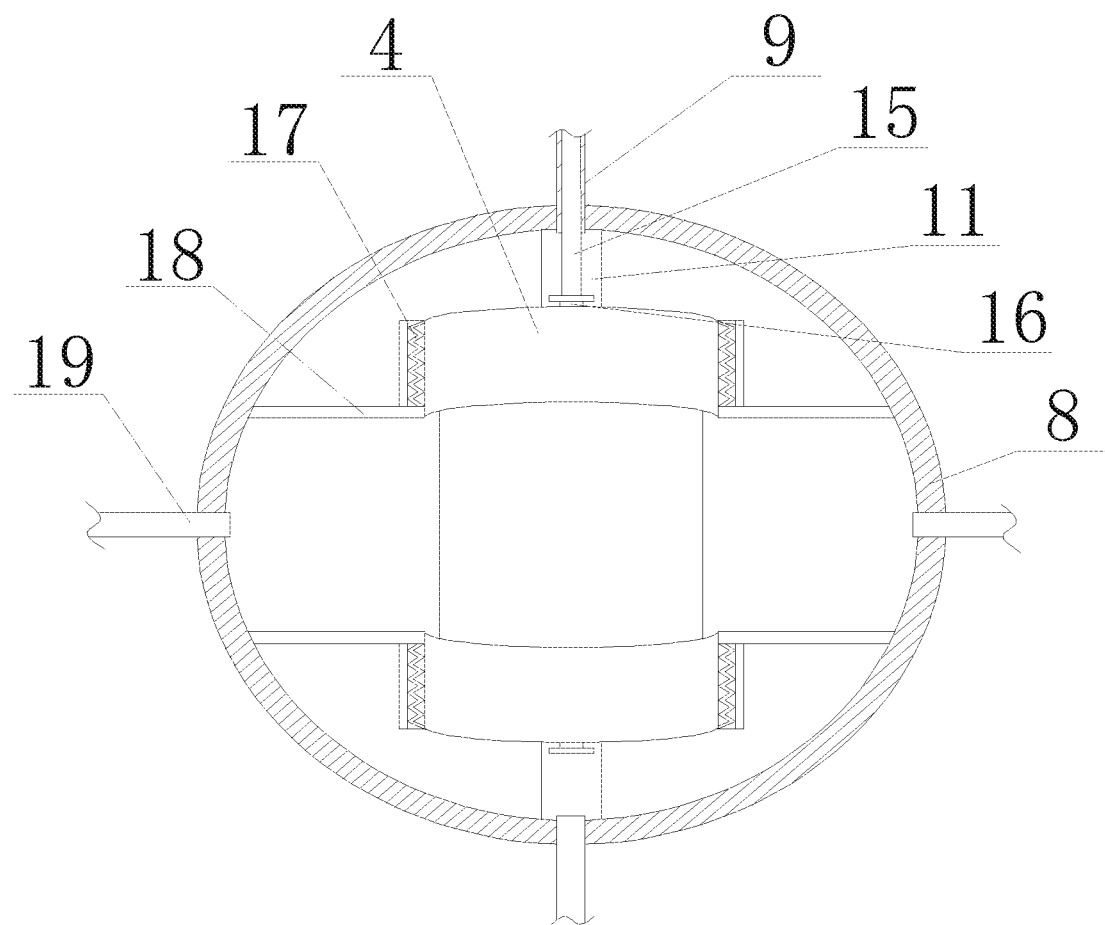
FIG. 2 is a transverse cross-sectional view of the present invention.
Figure 3:
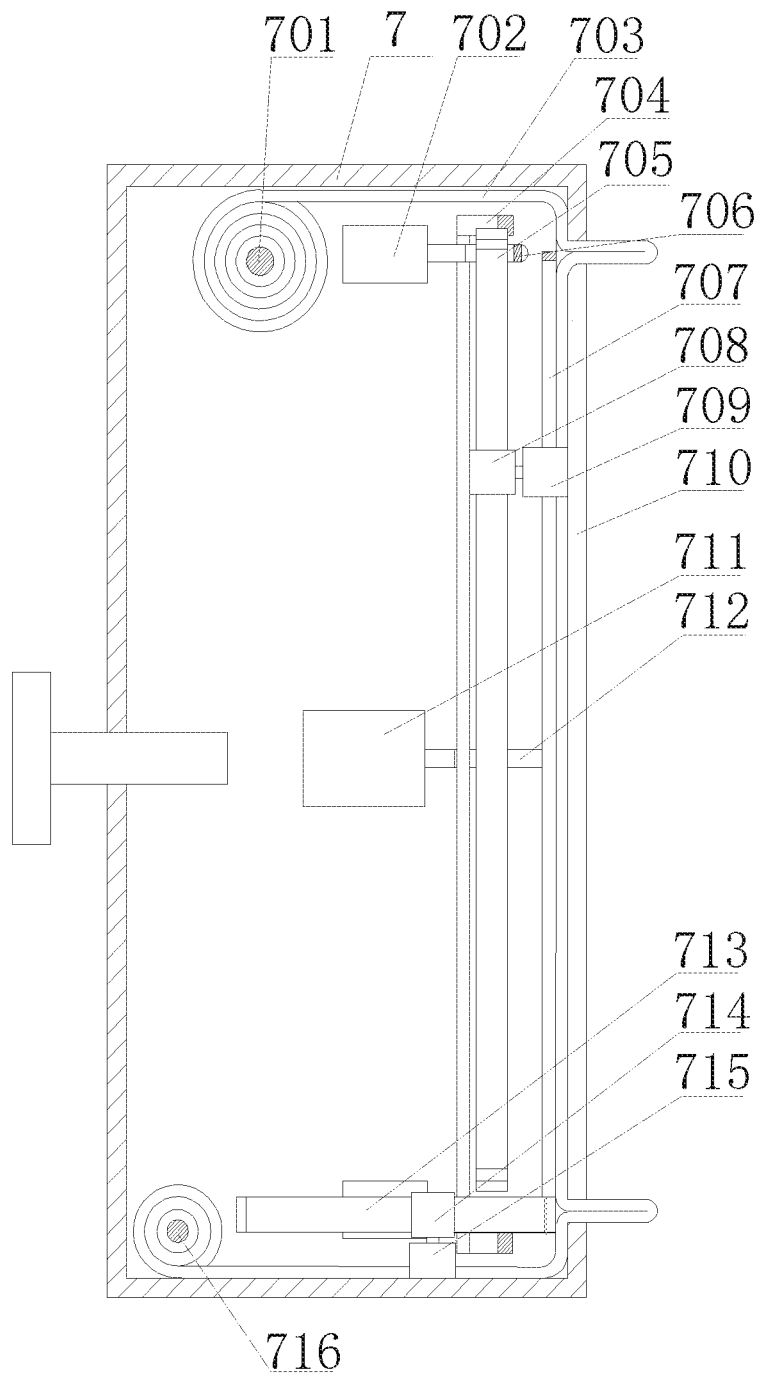
FIG. 3 is a structural view of a blocking mechanism I.
Figure 4:
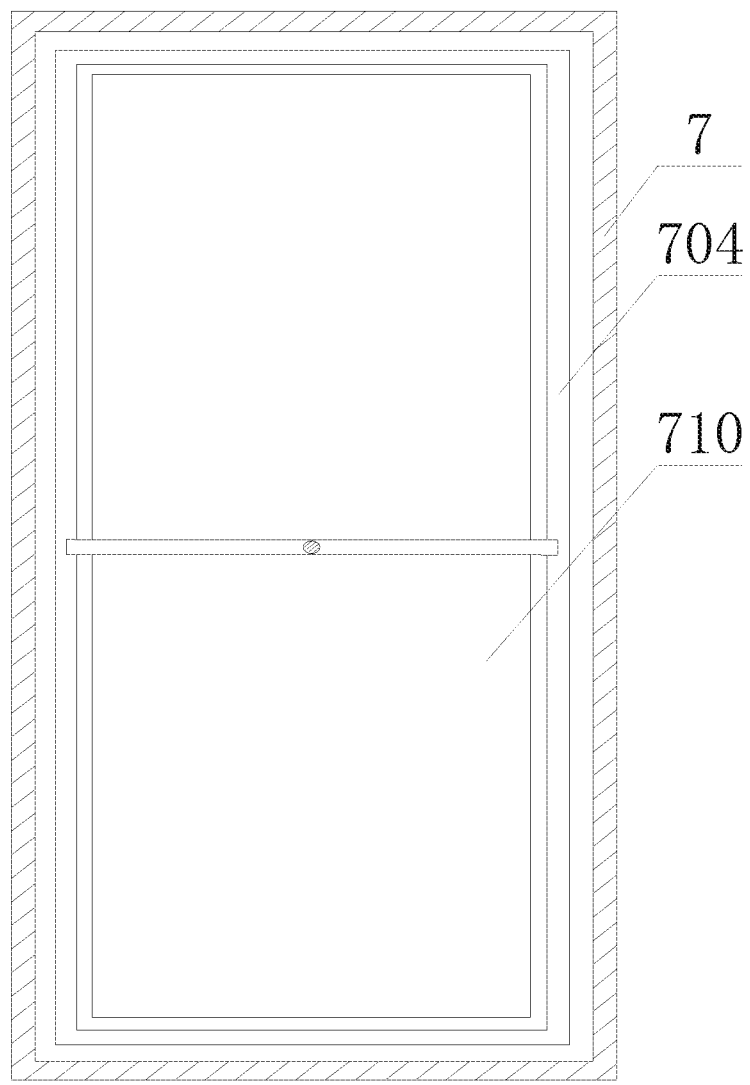
FIG. 4 is a side view of a pressing frame I in the block mechanism I.
Figure 5:
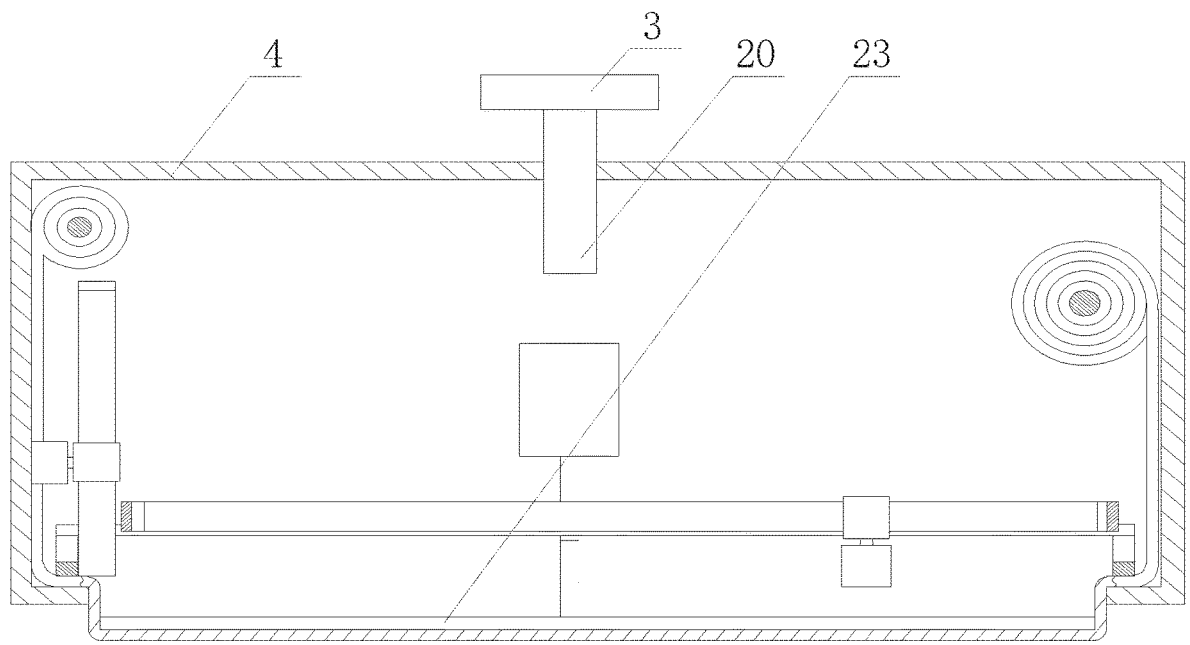
FIG. 5 is a structural view of a top blocking mechanism II.
Figure 6:
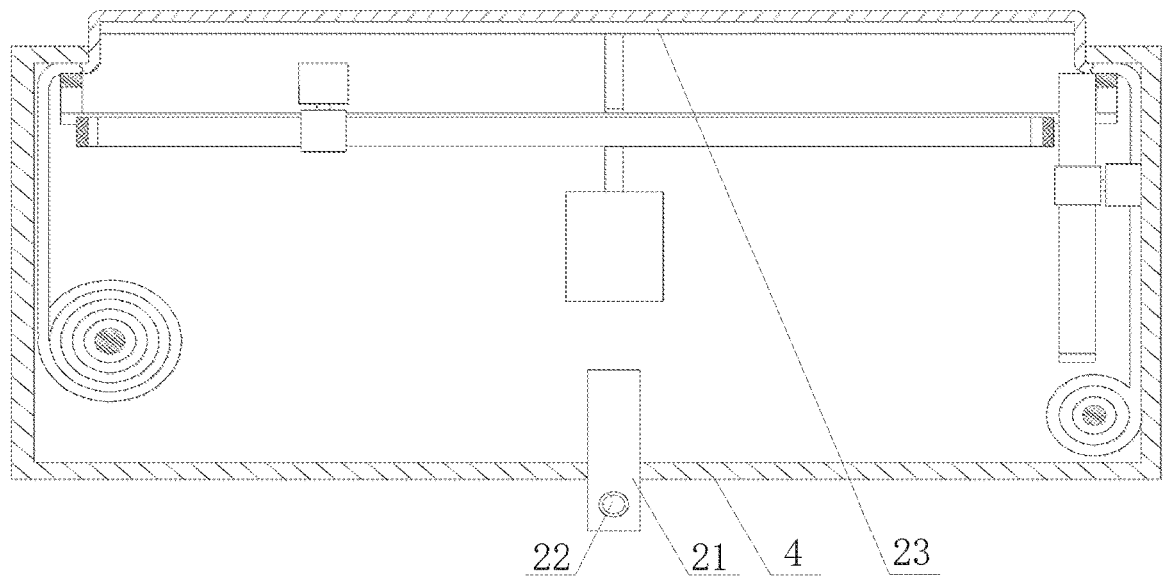
FIG. 6 is a structural view of a bottom blocking mechanism II.
Figure 7:
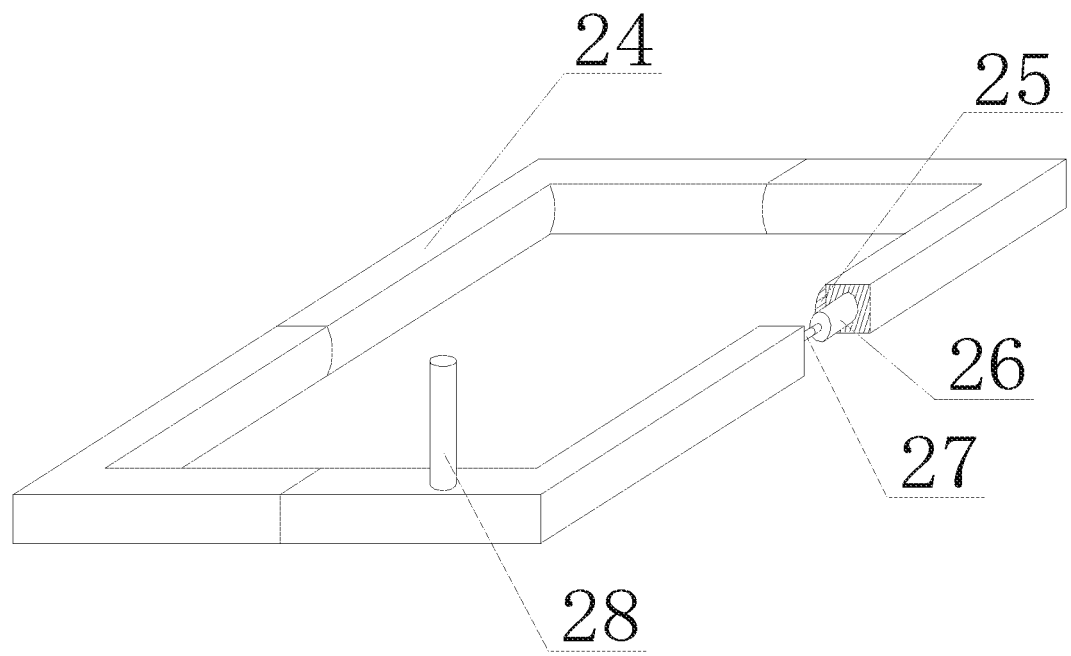
FIG. 7 is a structural view of the pressing frame I.
Figure 8:
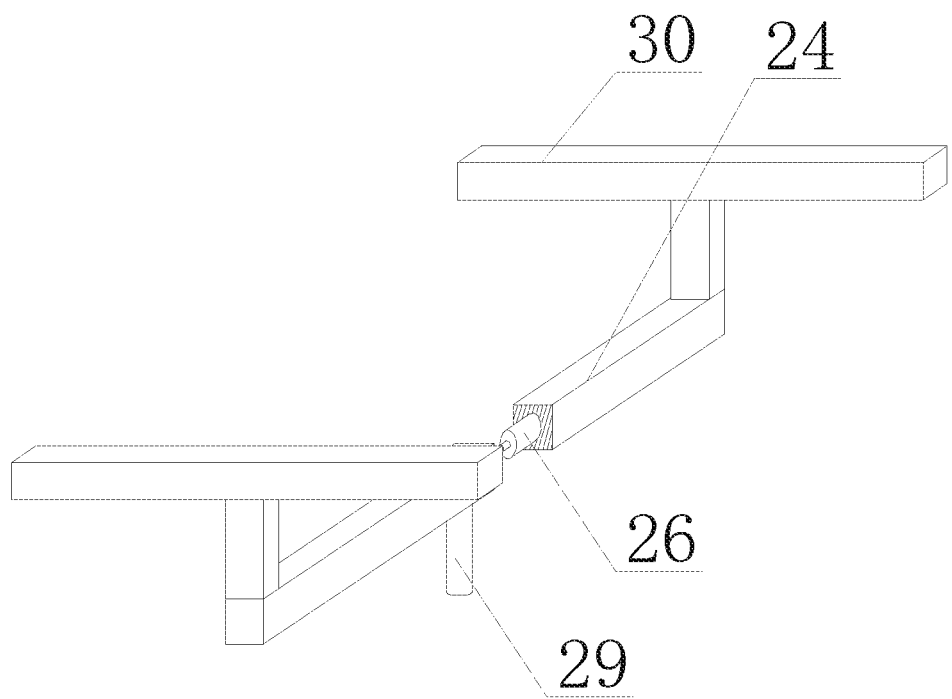
FIG. 8 is a structural view of a pressing frame II.
Figure 9:
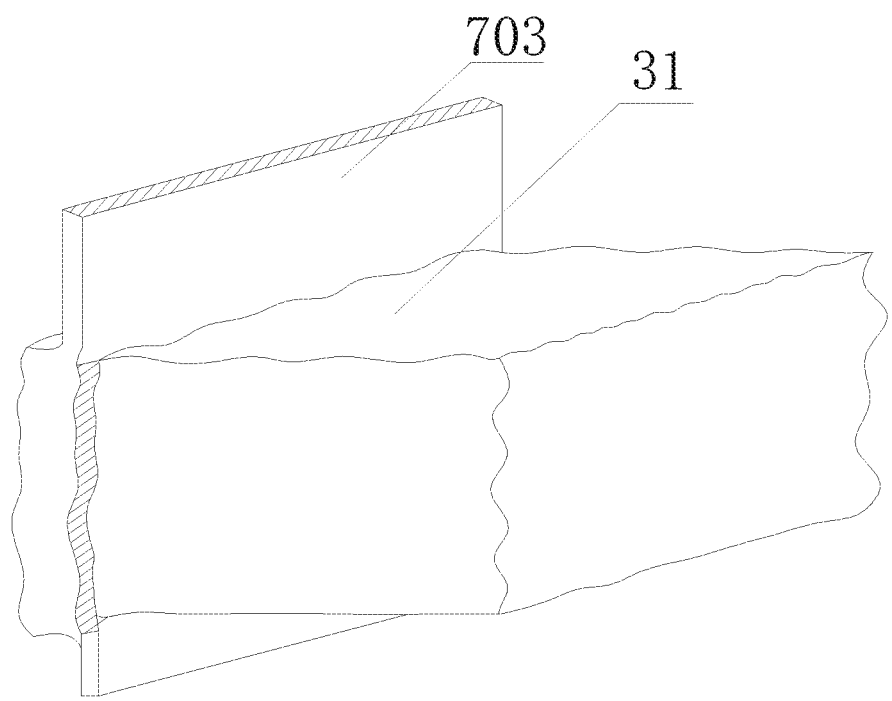
FIG. 9 is a structural view of a rock sample assembled with a water blocking film.
Figure 10:
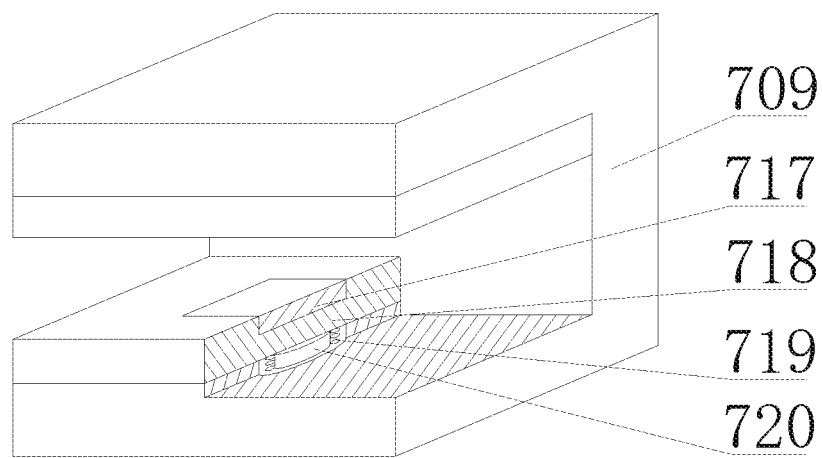
FIG. 10 is a structural view of a chuck.

Referring to FIGS. 1-10, the embodiment 1 comprises: a cylinder body 8 having a top opening, and a sealing cover 1 matched with the top opening of the cylinder body 8, wherein two blocking mechanisms I 7 are symmetrically arranged in the cylinder body 8 along an axis thereof, and two blocking mechanisms II 4 are respectively arranged at an internal top end and an internal bottom end of the cylinder body 8; partitioning plates 6, whose bottom ends are connected to a bottom of the cylinder body 8, are respectively arranged on both sides of each of the blocking mechanisms I 7; one end of a sealing organ cover 17 is connected to a sidewall of each of the partitioning plates 6, and the other end of the sealing organ cover 17 is connect a sidewall of each of the blocking mechanisms I 7; water blocking plates 18 are respectively arranged at both sides of each of the blocking mechanisms I 7 and are perpendicular to the partitioning plates 6; one end of each of the water blocking plates 18 is connected to the sidewall of each of the partitioning plates 6, and the other end of each of the water blocking plates 18 is connected to an internal portion of the cylinder body 8; a water injection pipe 19 is disposed between the water blocking plates 18 on a same side, and an end of the water injection pipe 19 extends outwardly through an internal wall of the cylinder body 8.

when the blocking mechanisms 17 and the blocking mechanisms II 4 block the rock sample, the water blocking film 703 is mainly applied to the non-permeable surfaces of the rock sample, and then the air pressure is synchronously added to the shell or the tank to ensure that the water blocking film 703 and the non-permeable surfaces are completely adhered to achieve seepage-proofing of the non-permeable surface. It should be noted that the structures of the blocking mechanisms 17 and the blocking mechanisms II 4 are substantially the same, such as the same size of the shell and the tank, as well as the corresponding size of the opening 710 and the through hole. In practice, the film assemblies are provided in the blocking mechanisms I 7 and the blocking mechanisms II 4. The film assembly of the blocking mechanisms I 7, for example, comprises the positive rotation shaft 701, the driving cylinder 711, the two longitudinal conveyor belts 705 and the two transverse conveyor belts 713, wherein the two longitudinal conveyor belts 705 are disposed on both side of the opening 710, and the two transverse conveyor belts 713 are disposed on the internal wall at the bottom of the shell; the water blocking film 703 is wound around the positive rotation shaft 701, and two sides thereof are respectively clamped through the first chucks 709 of the two longitudinal conveyor belts 705, so that the water blocking film 703 gradually seals the opening 710.

When the water blocking film 703 moves to the bottom of the shell, a first slider 708 is fixed on each of the longitudinal conveyor belts 705, a second slider 714 is fixed on each of the transverse conveyor belts 713, a first chuck 709 is fixed on the first slider 708, and a second chuck 715 is fixed on the second slider 714. When the movable end of the water blocking film 703 is moved to the horizontal position corresponding to the transverse conveyor belts 713, the first chuck 709 on each of the longitudinal conveyor belts 705 releases the water blocking film 703, while the second chuck 715 on each of the transverse conveyor belts 713 clamps the water blocking film 703 and moves the water blocking film 703 away from the opening 710 or the through hole; then the two horizontally placed push cylinders 702 are started, wherein the length of the push plate 706 equals to the width of the opening 710, which can drive the water blocking film 703 to extend outwardly through the opening 710. The extended portion of the water blocking film 703 can directly cover the top end surface and the bottom end surface of the rock sample. Then the driving cylinder 711 is started, and the output end of the driving cylinder 711 is provided with a pushing rod 712. The pushing rod 712 drives the rectangular frame 704 to press the water blocking film 703 until the rectangular frame 704 drives the water blocking film 703 to closely adhere to the internal wall of the shell, so as to seal the opening 710. At this time, the two ends of the rock sample are respectively supported by two openings 710.

After position adjustment of the blocking mechanisms II 4 located at the top and bottom ends of the rock sample, the internal film assembly starts to perform a filming action, and the film assembly in the blocking mechanisms II 4 performs the same action as that performed by the film assembly in the block mechanisms I 7, both close the through holes by the water blocking film 703 driven by the chucks on the two longitudinal conveyor belts 705 and the transverse lateral conveyor belts 713. Then the driving cylinder 711 in the tank is started, and the output end of the driving cylinder 711 drives the rectangular frame 704 to press the water blocking film 703 until the rectangular frame 704 drives the water blocking film 703 to closely adhere to the internal wall of the tank, so as to seal the through hole.

And the connecting tube 16 is disposed on the sidewall of the shell facing the opening 710, and the connecting tube 16 extends outwardly through the internal wall of the shell; the electromagnetic valve 3 is mounted on an extended end of the connecting tube 16; a sleeve II 9 is mounted on an external circumferential wall of the cylinder body 8, which communicates with the internal portion of the cylinder body 8; a communication tube 20 is disposed on a sidewall at a top of the rock sample 31, and the communication tube 20 extends outwardly through an internal wall of the tank; the electromagnetic valve 3 is also mounted on an extended end of the communication tube 20; a sleeve I 2 is mounted on a top end surface of the cylinder body 8, which communicates with the internal portion of the cylinder body 8; an intake pipe II moves through the sleeve I 2 and is connected to the electromagnetic valve 3; a straight tube 21 is disposed on a sidewall at a bottom of the internal portion of the cylinder body 8, and the straight tube 21 extends outwardly through the internal wall of the tank; a flexible hose 22 is connected to an extended end of the straight tube 21, and the flexible hose 22 extends outwardly through an external wall of the cylinder body 8. After driving the intake pipe I 15 and the intake pipe II to move, the two shells and the tank above the rock sample 31 can be linearly moved to adjust the position thereof, so as to match a shape of the rock sample to a maximum extent. Meanwhile, the tank below the rock sample remains stationary, and after the four water blocking films respectively contact with the four non-permeable surfaces of the rock sample, gas is simultaneously injected into the intake pipe I 15, the intake pipe II, and the hose 22, so that internal air pressures of the tank and the shell are increased to ensure that the water blocking film 703 is in close contact with each non-permeable surface. After the above steps are completed, water is injected into any one of the water injection pipes 19, and the other water injection pipes 19 are kept closed until the water level in the cylinder body 8 exceeds the bottom end of the tank above, and then the penetration test begins.

When the water blocking film 703 inside the two shells covers the sidewalls of the rock sample, under the pushing action of the push plate 706, the extended portion of the water blocking film 703 can partially cover the top and bottom end faces of the rock sample, while the water blocking film 703 at the two through holes covers the top and bottom end surfaces of the rock sample for the second time. At the same time, blocking effects on the four non-permeable surfaces of the rock sample are improved through extrusion of the air pressure in the tank.

Preferably, a reverse rotation shaft 716 is disposed inside the tank and the shell, and rotation directions of the reverse rotation shaft 716 and the positive rotation shaft 701 are the same. In practice, the positive rotation shaft 701 is rotatably installed, and the reverse rotation shaft 716 can be connected to an external driving device under the premise of active sealing. Furthermore, a main body of the water blocking film 703 is wound on the positive rotating shaft 701, and the extending end of the water blocking film 703 is connected to an external wall of the reverse rotation shaft 716. That is to say, when the non-permeable surfaces of the rock sample 31 are going to be switched and blocked by the water blocking film 703 after the first chuck 709 and the second chuck 715 both release the water blocking film 703, the reverse rotation shaft 716 can be used for winding the water blocking film 703, so as to improve the sealing effect after switching the non-permeable surfaces.

According to the embodiment 1, the water blocking film 703 is made of a BOPP film, namely a biaxially oriented polypropylene film, wherein a thickness is 20-45 μm, and a tensile strength satisfies MD MPa≥130, TD≥220; gas is injected into the shell and the tank, in such a manner that the water blocking film 703 is completely adhered to the permeable surfaces while integrity of the water blocking film 703 is ensured.

Embodiment 2

Referring to FIGS. 1-10, based on the embodiment 1, a pressing frame I 707 is disposed on the output end of the driving cylinder 711 inside the shell, and the pressing frame I 707 is a rectangular bracket formed by splicing four L-shaped plates 24; a telescopic cylinder 26 is mounted on one end surface of each of the L-shaped plates 24, and a connecting rod 27 is fixed on the other end surface; among adjacent L-shaped plates 24, an output end of the telescopic cylinder 26 of one L-shaped plate 24 is connected to the connecting rod 27 of the other L-shaped plate 24; a supporting rod 28 is respectively mounted on a sidewall of each of the L-shaped plates 24, and the supporting rod 28 is connected to the output end of the driving cylinder 711; a pressing frame II 23 is disposed on the output end of the driving cylinder 711 inside the tank, and the pressing frame II 23 is a U-shaped bracket formed by splicing two symmetrically distributed L-shaped plates 24; the telescopic cylinder 26 is mounted on an end surface of a horizontal section of one L-shaped plate 24, and the connecting rod 27 is mounted on an end surface of a horizontal section of the other L-shaped plate 24; the output end of the telescopic cylinder 26 is connected to the connecting rod 27; a vertical end face of each of the L-shaped plates 24 is provided with a pressing rod 30, and the pressing rod 30 is perpendicular to a vertical section of the L-shaped plates 24; a strut 29 is provided on any one of the L-shaped plates 24, and is connected to the output end of the driving cylinder 711.

Since edges of the square rock sample are not straight lines, the applicant provides the pressing frame I 707 and the pressing frame II 23 respectively in the shell and the tank, which means the pressing frame 1707 corresponds to the rectangular bracket and the pressing frame II 23 corresponds to the U-shaped bracket. When the water blocking film 703 blocks the four non-permeable surfaces, the rectangular bracket and the U-shaped bracket can drive the water blocking film 703 to completely wrap the non-permeable surfaces, and can expand and contract to a certain amplitude, so as to allow corner portions of the two end faces to be tested of the rock sample 31 to be wrapped by the water blocking film 703 to prevent water penetrating along the non-permeable surfaces, thereby ensuring the accuracy of the test data.

In practice, the rectangular frame 704 and the rectangular bracket are both fixed on the output end of the driving cylinder 711 in the shell, and an interval between the rectangular bracket and the opening 710 is smaller than an interval between the rectangular frame 704 and the opening 710. That is to say, when the driving cylinder 711 is started, the rectangular bracket first drives the water blocking film 703 to pass through the opening 710 and then to be sleeved at an end of the rock sample 31, wherein the rectangular bracket is formed by splicing four L-shaped plates 24, and among adjacent L-shaped plates 24, the output end of the telescopic cylinder 26 of one L-shaped plate 14 is connected to the connecting rod 27 of the other L-shaped plate 24, which allows an operator to adjust length and width of the rectangular bracket according to an actual size of the rock sample, and to finally ensure that the rectangular bracket can drive the water blocking film 703 to completely wrap the non-permeable surfaces of the rock sample to avoid permeation of the non-permeable surfaces. The rectangular frame 704 and the U-shape bracket are both fixed on the output end of the driving cylinder 711 in the tank, and an interval between the U-shape bracket and the opening 710 is smaller than an interval between the rectangular frame 704 and the opening 710. That is to say, when the driving cylinder 711 is started, the rectangular bracket first drives the water blocking film 703 to pass through the opening 710 and then to be sleeved at an end of the rock sample 31, wherein the U-shape bracket is formed by splicing two L-shaped plates 24, and the telescopic cylinder 26 is mounted on the end surface of the horizontal section of one L-shaped plate 24, and the connecting rod 27 is mounted on the end surface of the horizontal section of the other L-shaped plate 24; the output end of the telescopic cylinder 26 is connected to the connecting rod 27; the vertical end face of each of the L-shaped plates 24 is provided with the pressing rod 30, and the pressing rod 30 is perpendicular to the vertical section of the L-shaped plates 24. Similarly, the operator can adjust an interval between the pressing rod 30 according to the actual size of the rock sample 31, to finally ensure that the U-shape bracket can drive the water blocking film 703 to completely wrap the non-permeable surfaces of the rock sample to avoid permeation of the non-permeable surfaces.

Embodiment 3

Referring to FIGS. 1-10, a function of the first chuck 709 is to move the water blocking film 703 along a fixed track in a lateral direction or a longitudinal direction, and since the water blocking film 703 belongs to a flexible material, the first chuck 709 should provide sufficient clamping force while ensures accurate clamping or releasing of the water blocking film 703. Therefore, the applicant sets the U-shaped body and the two flexible splints 718. In an initial state, the two flexible splints 718 are in contact with each other, and the torsion spring 719 is in a free state. When the first chuck 709 needs to be contacted to hold the water blocking film 703, the electromagnets 717 on the two flexible splints 718 are simultaneously energized to have same magnetic poles, wherein repulsive force is generated between the two electromagnets 717, so that the flexible splints 718 press and compress the torsion spring 719, and an interval between the two flexible splints 718 is increased, which means the first chuck 709 releases the water blocking film 703. The electromagnet 717 is turned on and off to provide smooth transition from longitudinal movement to lateral movement of the water block film 703, avoiding a situation that the four first chucks 709 simultaneously clamp and pull the water blocking film 703 during use. Water blocking film integrity throughout the test is ensured.

According to the embodiment 3, a circular bottom plate 12 is disposed at a bottom portion of the internal wall of the cylinder body 8, and the circular bottom plate divides the internal portion of the cylinder body into an adjustment zone and a test zone which are independent. After being placed in the cylinder body 8, the rock sample 31 is supported by the blocking mechanisms II 4 at the bottom of the cylinder body 8. And before testing, relative positions of the two blocking mechanisms I 7 and the two blocking mechanisms II 4 need to be adjusted to ensure the blocking effect of the four non-permeable surfaces the rock sample 31. When the blocking mechanisms II 4 located at the bottom of the cylinder body 8 are lifted or lowered, only the up-push cylinder 14 is activated, and the top end of the ram at the output end of the up-push cylinder 14 moves through the waterproof ring 13 and then is connected to an external wall of the blocking mechanisms II 4 located at a bottom of the test zone. When the output end of the up-push cylinder 14 drives the ram to move, the tank can be driven to move linearly. The waterproof ring 14 is a waterproof rubber ring. Under the premise of relative motion between the waterproof rubber ring and the ram, the independence between the test zone and the adjustment zone can be ensured.

Preferably, since the two shells need to be positionally adjusted before the test; that is, the shell will move linearly, the guide rails 11 are fixed inside the cylinder body 8 by the applicant to improve stability of the shell movement, and each of the guild rails 11 is respectively located between the partitioning plates 6 of the same side; the sliding groove is provided on the top surface of each of the guide rails 11, and the guiding block 10 cooperating with the sliding groove is provided at the bottom of the shell. The guiding block 10 can only move along a trajectory where the sliding groove is located, which lowers a possibility of shell sloshing and ensures shell stability when it is adjusted from an initial position to a final state, thereby ensuring the sealing effect on the four non-permeable surfaces of the rock sample.

Preferably, a rubber pad 25 having an arcuate cross section is provided on each internal sidewall of the rectangular frame, so that the rectangular frame realizes flexible contact when the water blocking film 703 is wrapped around the rock sample, and reduces mutual damages between the water blocking film 703 and the rock sample 31 when the rectangular frame contracts.

Embodiment 4

Referring to FIGS. 1-10, the embodiment 4 comprises steps of:

a) clearing soil and fragmented rocks deposited by weathering and erosion on a surface of a rock mass to be investigated, excavating vertical trenches around a target point, and exposing a fresh geological body to be inspected;

b) using a joint structure analysis method together with a geophysical detection method to extract fracture intersection information inside the geological body exposed in the step a), and identifying water-conducting units and water-control nodes which conduct and control a groundwater flow;

c) based on an identification result of the step b), marking four to five sampling ranges on the geological body to be inspected which is obtained in the step a), and intercepting large-volume irregular undisturbed rock samples 31 containing a plurality of the water-conducting units and water-control nodes along each sampling boundary;

d) determining four to five seepage test directions for the rock samples 31 obtained in the step c), and defining two opposite boundaries along a sample seepage direction as permeable interfaces A and B, wherein A is an in-permeation surface, B is an out-permeation surface, and other sample boundary surfaces are defined as non-permeable surfaces;

e) loading one of the rock samples 31 in the step d) into a cylinder body 8 according to a position meeting a predetermined seepage direction, in such a manner that the in-permeation surface and the out-permeation surface of the rock sample 31 respectively correspond to two open end faces of the cylinder body 8; blocking the non-permeable surfaces by two blocking mechanism I 7 and two blocking mechanisms II 4;

f) waiting until an anti-seepage blocking treatment in the step e) is completed, then sealing the open ends of the cylinder body 8 by sealing covers 1 to form a seepage pressure chamber;

g) connecting an in-permeation surface of the seepage pressure chamber to a pressurized water supply equipment through a water injection pipe 19, and connecting an out-permeation surface to a water storage container through another water injection pipe 19, so as to assemble an irregular rock sample high-pressure permeation tester;

h) after components in the step g) are completely connected, staring a pressure measuring device to apply an osmotic water pressure to the rock sample 31 when air pressures in two shells and two tanks reach a steady state, wherein water continuously flows along a fracture network of the rock sample 31 from the in-permeation surface under a preset initial pressure, so as to achieve sample saturation;

i) adjusting an osmotic pressure value of the pressure measuring equipment, and recording corresponding data comprising pressures, times and flow rates after water flow reaches a steady state; further changing a confining pressure and the osmotic pressure value according to a predetermined plan in an experimental scheme, to obtain a group of steady-state test data corresponding to different confining pressures and different osmotic pressures;

j) opening the sealing covers 1, and releasing the two blocking mechanisms I 7 and the two blocking mechanisms II 4 to free the non-permeable surfaces of the rock sample 31; turning the rock sample 31, and redefining the non-permeable surfaces, the in-permeation surface and the out-permeation surface of the rock sample 31 according to the seepage test directions determined in the step d); repeating the steps e)-i) until the rock sample 31 seeps through all the predetermined seepage test directions;

k) repeating the steps d)-j) for the other of the rock samples 31 obtained in the step c) until all the rock samples 31 are tested; and l) calculating and analyzing based on data obtained in the step k) to obtain spatial variability of a water-conducting structure of a geological structure under different seepage pathways, and further obtain comprehensive characterization results of hydrogeological properties of the geological structure.

During the test, the surface of the rock sample 31 is irregularly undulated, but in the field sampling, the rock sample 31 of the approximate square shape should be taken as the sample to be tested, and the six faces of the rock sample 31 are defined as three sets of independent interfaces. When one set is selected as the water permeable surfaces, the remaining two sets are the non-permeable surfaces to be blocked, and the blocking action is performed by the blocking mechanisms I 7 and the blocking mechanism II 4. in order to meet requirement of water conductivity difference analysis under the different seepage pathways, the boundary conditions of different sets of independent surfaces are flexibly switched between permeable and non-permeable by turning the rock sample 31, and the penetration test along different directions of the rock sample 31 is carried out to obtain spatial variability of hydraulic parameters of geological structures.

What is claimed is:

1. An irregular rock sample high-pressure permeation device with an adjustable flow direction, comprising: a cylinder body (8) having a top opening, and a sealing cover (1) matched with the top opening of the cylinder body (8), wherein two blocking mechanisms I (7) are symmetrically arranged in the cylinder body (8) along an axis thereof, and two blocking mechanisms II (4) are respectively arranged at an internal top end and an internal bottom end of the cylinder body (8); partitioning plates (6), whose bottom ends are connected to a bottom of the cylinder body (8), are respectively arranged on both sides of each of the blocking mechanisms I (7); one end of a sealing organ cover (17) is connected to a sidewall of each of the partitioning plates (6), and the other end of the sealing organ cover (17) is connect a sidewall of each of the blocking mechanisms I (7); water blocking plates (18) are respectively arranged at both sides of each of the blocking mechanisms I (7) and are perpendicular to the partitioning plates (6); one end of each of the water blocking plates (18) is connected to the sidewall of each of the partitioning plates (6), and the other end of each of the water blocking plates (18) is connected to an internal portion of the cylinder body (8); a water injection pipe (19) is disposed between the water blocking plates (18) on a same side, and an end of the water injection pipe (19) extends outwardly through an internal wall of the cylinder body (8); during utilization, an irregular rock sample is placed in the cylinder body (8), and the two blocking mechanisms I (7) and the two blocking mechanisms II (4) are adjusted to block four sidewalls of the irregular rock sample, while two sides of the irregular rock sample, which face the water injection pipe (19), are not blocked.

2. The irregular rock sample high-pressure permeation device, as recited in claim 1, wherein a circular bottom plate (12) is disposed at a bottom portion of the internal wall of the cylinder body (8), and the circular bottom plate (12) divides the internal portion of the cylinder body (8) into an adjustment zone and a test zone which are independent; an up-push cylinder (14) is disposed in the adjustment zone, and a ram is provided at an output end of the up-push cylinder (14); a small hole is opened in a middle of the circular bottom plate (12), and a waterproof ring (13) is installed in the small hole; a top end of the ram moves through the waterproof ring (13) and then is connected to an external wall of the blocking mechanisms II (4) located at a bottom of the test zone.

3. The irregular rock sample high-pressure permeation device, as recited in claim 1, wherein each of the blocking mechanisms I (7) comprises a shell having a cavity therein, wherein an opening (710) is provided on a sidewall of the shell; each of the blocking mechanisms II (4) comprises a tank having a cavity therein, wherein a through hole is provided on a sidewall of the tank; film assemblies are disposed inside the shell as well as the tank, comprising a positive rotation shaft (701), a driving cylinder (711), two longitudinal conveyor belts (705) and two transverse conveyor belts (713), wherein a water blocking film (703) is wound around an external circumferential wall of the positive rotation shaft (701), and the longitudinal conveyor belts (705) are perpendicular to the transverse conveyor belts (713); a first slider (708) is fixed on each of the longitudinal conveyor belts (705), a second slider (714) is fixed on each of the transverse conveyor belts (713), a first chuck (709) is fixed on the first slider (708), and a second chuck (715) is fixed on the second slider (714); an output end of the driving cylinder (711) is provided with a rectangular frame (704); the positive rotating shaft (701) is rotatably disposed at a top of an internal wall of the shell; the two longitudinal conveyor belts (705) are located at two sides of the opening (710) or the through hole, and a movable end of the water blocking film (703) gradually closes the opening (710) or the through hole with clamping of the first chuck (709) on each of the longitudinal conveyor belts (705); when the movable end of the water blocking film (703) is moved to a horizontal position corresponding to the transverse conveyor belts (713), the first chuck (709) on each of the longitudinal conveyor belts (705) releases the water blocking film (703), while the second chuck (715) on each of the transverse conveyor belts (713) clamps the water blocking film (703) and moves the water film (703) away from the opening (710) or the through hole; then the driving cylinder (711) is started, and the output end of the driving cylinder (711) drives the rectangular frame (704) to press the water blocking film (703), so as to seal the opening (710) or the through hole;
a connecting tube (16) is disposed on a sidewall of the shell facing the opening (710), and the connecting tube (16) extends outwardly through the internal wall of the shell; an electromagnetic valve (3) is mounted on an extended end of the connecting tube (16); a sleeve II (9) is mounted on an external circumferential wall of the cylinder body (8), which communicates with the internal portion of the cylinder body (8); an intake pipe I(15) moves through the sleeve II (9) and is connected to the electromagnetic valve (3);
a communication tube (20) is disposed on a sidewall at a top of the internal portion of the cylinder body (8), and the communication tube (20) extends outwardly through an internal wall of the tank; the electromagnetic valve (3) is also mounted on an extended end of the communication tube (20); a sleeve I (2) is mounted on a top end surface of the cylinder body (8), which communicates with the internal portion of the cylinder body (8); an intake pipe II moves through the sleeve I (2) and is connected to the electromagnetic valve (3);
a straight tube (21) is disposed on a sidewall at a bottom of the internal portion of the cylinder body (8), and the straight tube (21) extends outwardly through the internal wall of the tank; a flexible hose (22) is connected to an extended end of the straight tube (21), and the flexible hose (22) extends outwardly through an external wall of the cylinder body (8);
two push cylinders (702) are horizontally placed in the shell, and an output end of each of the push cylinders (702) is mounted with a push plate (706) perpendicular to the longitudinal conveyor belts (705), wherein a length of the push plate (706) equals to a width of the opening (710), and an interval between two push plates (706) equals to a length of the opening (710).

4. The irregular rock sample high-pressure permeation device, as recited in claim 3, wherein the first chuck (709) comprises a U-shaped body and two flexible splints (718), wherein blind holes are drilled on sidewalk corresponding to two vertical sections of the U-shaped body; a pin (720) is mounted on one sidewall of each of the flexible splints (718), and an electromagnet (717) is embedded in a middle of the other sidewall of each of the flexible splints (718); a gap is left between an end face of the pin (720) and a bottom of the blind hole, and a torsion spring (719) is sleeved on an external circumferential wall the pin (720); one end of the torsion spring (719) is connected to the external circumferential wall of the pin (720), and the other end of the torsion spring (719) is connected to the bottom of the blind hole.

5. The irregular rock sample high-pressure permeation device, as recited in claim 3, wherein two guide rails (11) are fixed on the internal wall of the cylinder body (8), and each of the guild rails (11) is respectively located between the partitioning plates (6) of a same side; a sliding groove is provided on a top surface of each of the guide rails (11), and a guiding block (10) cooperating with the sliding groove is provided at a bottom of the shell.

6. The irregular rock sample high-pressure permeation device, as recited in claim 3, wherein a pressing frame I (707) is disposed on the output end of the driving cylinder (711) inside the shell, and the pressing frame I (707) is a rectangular bracket formed by splicing four L-shaped plates (24); a telescopic cylinder (26) is mounted on one end surface of each of the L-shaped plates (24), and a connecting rod (27) is fixed on the other end surface; among adjacent L-shaped plates (24), an output end of the telescopic cylinder (26) of one L-shaped plate (24) is connected to the connecting rod (27) of the other L-shaped plate (24); a supporting rod (28) is respectively mounted on a sidewall of each of the L-shaped plates (24), and the supporting rod (28) is connected to the output end of the driving cylinder (711);
a pressing frame II (23) is disposed on the output end of the driving cylinder (711) inside the tank, and the pressing frame II (23) is a U-shaped bracket formed by splicing two symmetrically distributed L-shaped plates (24); the telescopic cylinder (26) is mounted on an end surface of a horizontal section of one L-shaped plate (24), and the connecting rod (27) is mounted on an end surface of a horizontal section of the other L-shaped plate (24); the output end of the telescopic cylinder (26) is connected to the connecting rod (27); a vertical end face of each of the L-shaped plates (24) is provided with a pressing rod (30), and the pressing rod (30) is perpendicular to a vertical section of the L-shaped plates (24); a strut (29) is provided on any one of the L-shaped plates (24), and is connected to the output end of the driving cylinder (711).

7. The irregular rock sample high-pressure permeation device, as recited in claim 6, wherein a rubber pad (25) having an arcuate cross section is provided on each internal sidewall of the rectangular frame (704).

8. A test method of an irregular rock sample high-pressure permeation device with an adjustable flow direction, comprising steps of:
- a) clearing soil and fragmented rocks deposited by weathering and erosion on a surface of a rock mass to be investigated, excavating vertical trenches around a target point, and exposing a fresh geological body to be inspected;
- b) using a joint structure analysis method together with a geophysical detection method to extract fracture intersection information inside the geological body exposed in the step a), and identifying water-conducting units and water-control nodes which conduct and control a groundwater flow;
- c) based on an identification result of the step b), marking four to five sampling ranges on the geological body to be inspected which is obtained in the step a), and intercepting large-volume irregular undisturbed rock samples (31) containing a plurality of the water-conducting units and water-control nodes along each sampling boundary;
- d) determining four to five seepage test directions for the rock samples (31) obtained in the step c), and defining two opposite boundaries along a sample seepage direction as permeable interfaces A and B, wherein A is an in-permeation surface, B is an out-permeation surface, and other sample boundary surfaces are defined as non-permeable surfaces;
- e) loading one of the rock samples (31) in the step d) into a cylinder body (8) according to a position meeting a predetermined seepage direction, in such a manner that the in-permeation surface and the out-permeation surface of the rock sample (31) respectively correspond to two open end faces of the cylinder body (8); blocking the non-permeable surfaces by two blocking mechanism I (7) and two blocking mechanisms II (4);
- f) waiting until an anti-seepage blocking treatment in the step e) is completed, then sealing the open ends of the cylinder body (8) by sealing covers (1) to form a seepage pressure chamber;
- g) connecting an in-permeation surface of the seepage pressure chamber to a pressurized water supply equipment through a water injection pipe (19), and connecting an out-permeation surface to a water storage container through another water injection pipe (19), so as to assemble an irregular rock sample high-pressure permeation tester;
- h) after components in the step g) are completely connected, staring a pressure measuring device to apply an osmotic water pressure to the rock sample (31) when air pressures in two shells and two tanks reach a steady state, wherein water continuously flows along a fracture network of the rock sample (31) from the in-permeation surface under a preset initial pressure, so as to achieve sample saturation;
- i) adjusting an osmotic pressure value of the pressure measuring equipment, and recording corresponding data comprising pressures, times and flow rates after water flow reaches a steady state; further changing a confining pressure and the osmotic pressure value according to a predetermined plan in an experimental scheme, to obtain a group of steady-state test data corresponding to different confining pressures and different osmotic pressures;
- j) opening the sealing covers (1), and releasing the two blocking mechanisms I (7) and the two blocking mechanisms II (4) to free the non-permeable surfaces of the rock sample (31); turning the rock sample (31), and redefining the non-permeable surfaces, the in-permeation surface and the out-permeation surface of the rock sample (31) according to the seepage test directions determined in the step d); repeating the steps e)-i) until the rock sample (31) seeps through all the predetermined seepage test directions;
- k) repeating the steps d)-j) for the other of the rock samples (31) obtained in the step c) until all the rock samples (31) are tested; and
- l) calculating and analyzing based on data obtained in the step k) to obtain spatial variability of a water-conducting structure of a geological structure under different seepage pathways, and further obtain comprehensive characterization results of hydrogeological properties of the geological structure.

* * * * *